United States Patent
Panattoni et al.

(10) Patent No.: US 7,384,528 B2
(45) Date of Patent: *Jun. 10, 2008

(54) COATING OF PRE-CAST ELECTROPHORESIS SLAB GELS

(75) Inventors: Cory M. Panattoni, Winters, CA (US); Lee Olech, Rodeo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 686 days.

This patent is subject to a terminal disclaimer.

(21) Appl. No.: 10/746,453

(22) Filed: Dec. 23, 2003

(65) Prior Publication Data

US 2004/0134784 A1  Jul. 15, 2004

Related U.S. Application Data

(63) Continuation of application No. 09/973,179, filed on Oct. 5, 2001, now Pat. No. 6,743,344.

(60) Provisional application No. 60/241,381, filed on Oct. 17, 2000.

(51) Int. Cl.
*G01N 27/453* (2006.01)

(52) U.S. Cl. ........................... 204/616; 204/618

(58) Field of Classification Search ............... 204/616, 204/456–470, 606–621
See application file for complete search history.

(56) References Cited

U.S. PATENT DOCUMENTS

| | | | | |
|---|---|---|---|---|
| 3,975,162 | A * | 8/1976 | Renn | 436/169 |
| 4,897,306 | A * | 1/1990 | Sugimoto et al. | 204/616 |
| 5,324,412 | A * | 6/1994 | Kolner | 204/619 |
| 5,935,401 | A * | 8/1999 | Amigo | 204/454 |
| 5,938,906 | A * | 8/1999 | Moi et al. | 204/465 |
| 6,013,165 | A | 1/2000 | Wiktorowicz et al. | |
| 6,056,860 | A * | 5/2000 | Amigo et al. | 204/454 |
| 6,277,259 | B1 * | 8/2001 | Guttman et al. | 204/461 |
| 6,521,111 | B1 * | 2/2003 | Amshey et al. | 204/616 |
| 6,743,344 | B2 * | 6/2004 | Panattoni et al. | 204/615 |

* cited by examiner

*Primary Examiner*—Alex Noguerola
(74) *Attorney, Agent, or Firm*—Townsend and Townsend and Crew LLP.; Henry Heines

(57) ABSTRACT

In pre-cast slab gel cassettes, the formation of pathways in which proteins can migrate between the gel and the walls of the cassette to form shadow bands is avoided by the application of a coating of a nonionic amphiphilic polymer to the cassette walls. The coating also prevents the gel from sticking to the walls when the gel is to be removed from the cassette after electrophoresis.

4 Claims, No Drawings

COATING OF PRE-CAST ELECTROPHORESIS SLAB GELS

CROSS-REFERENCE TO RELATED APPLICATIONS

This application is a continuation of application Ser. No. 09/973,179, filed Oct. 5, 2001, now U.S. Pat. No. 6,743,344, is related to and claims the benefit of U.S. provisional patent application No. 60/241,381, filed Oct. 17, 2000, for all legal purposes capable of being served thereby. The contents of both provisional patent application No. 60/241,381 and application Ser. No. 09/973,179 are incorporated herein by reference in their entirety.

BACKGROUND OF THE INVENTION

This invention relates to polyacrylamide gels as used in slab gel electrophoresis.

Slab gels are particularly useful for electrophoresis in view of their ability to accommodate multiple sample analyses and the ease with which the electropherograms can be observed and read visually by identifying the locations of the various bands on the gels that correspond to the individual components. Polyacrylamide is a gel material that is widely used in slab gels.

Slab gels are frequently supplied in pre-cast form, retained between two flat transparent plates in a cassette. The plates may be glass or plastic, a common plastic being a polystyrene-acrylonitrile blend. A difficulty with certain pre-cast polyacrylamide gels is that they appear to separate from the cassette plates during storage, leaving a pathway between the gel and one or both of the plates for the sample to migrate. This apparent pathway is detrimental to the electrophoretic analysis since the solute bands in the gel tend to migrate into the pathway and spread, forming shadow bands. A shadow band is a band of protein that results from the migration of protein away from a parent protein band during electrophoresis, the parent protein band being the well-defined band that is formed as a direct result of the electrophoretic separation. Shadow bands reside mostly on the surface of the gel, whereas the parent protein bands extend relatively uniformly through the thickness of the gel. The pathways and shadow bands decrease the shelf life of precast gels and can eventually evolve into a smear of protein on the surface of the gel. The shadow bands are a particular problem in pre-cast gels that have been stored without cooling.

Another problem encountered with polyacrylamide slab gels is a tendency of the gels to stick or adhere to the plates. This presents a difficulty once the separation has been performed and the user attempts to remove the gel from the plate for purposes of staining, photographing or other observation, detection or recordation. Attempts to remove a gel that is sticking to one or both of the plates can result in a damaged gel and a ruined experiment. This problem is especially acute for gels of low concentration and for gels used for isoelectric focusing.

The polymerization reaction to form polyacrylamide is inhibited when dissolved oxygen is present in the gel-forming liquid at or near the gel plate. This is especially true when the gel plates are plastic, such as polystyrene-acrylonitrile, for example. To prevent this inhibition from occurring, a coating of polyvinylidene chloride or polyvinyl dichloride (PVDC) is often applied to the plates prior to contacting the plates with the polyacrylamide gel material. Unfortunately, these coatings produce an effect on the electrophoresis image that appears to be the result of separation between the gel and the plate. These coatings also exacerbate the sticking problem when the gel is an isoelectric focusing gel, for example one with a pH ranging from 5 to 8.

SUMMARY OF THE INVENTION

The present invention resides in the discovery that both the occurrence of what appear to be pathways between a polyacrylamide gel and a gel cassette plate and the adherence of the gel to the plate can be prevented by applying a coating of a nonionic amphiphilic polymer to the plate surface before the gel is cast. The coating may be applied directly to the surface of the glass or plastic plate or it may be applied over a polyvinylidene chloride or polyvinyl dichloride coating if such a coating is present. Once the gels are formed over the coating, the gels can be stored for extended periods of time with no extraneous path formation or sticking problem.

DETAILED DESCRIPTION OF THE INVENTION AND PREFERRED EMBODIMENTS

Examples of nonionic amphiphilic polymers that can be used as coating materials in the practice of this invention are polyvinyl alcohol, agarose, polyvinyl pyrrolidone, polyethylene glycol, polypropylene glycol, polypropylene glycol/polyethylene glycol copolymers, and linear polyacrylamide. Polyvinyl alcohol of 14,000 molecular weight (weight-average) for example can be applied as a 1% (by weight) aqueous solution. For polyvinyl alcohol use in general, a weight-average molecular weight ranging from about 10,000 to about 100,000 may be applied as an aqueous solution of concentration ranging from about 0.5% to saturation. For coatings of polyethylene glycol, an example is one with a weight-average molecular weight of about 20,000, or a range of from about 10,000 to about 100,000. The polyethylene glycol can be applied as a 1-4% (by weight) aqueous solution. The concentrations and molecular weights of other polymers are readily determined by routine experimentation and will in many cases be readily apparent to those skilled in the art.

The nonionic amphiphilic polymer solution can be applied by any means that will result in a substantially even distribution over the plate surface and a clear film. Examples of application techniques are spin coating, dip coating, and brush coating. Once the film is applied, it can be dried by conventional techniques before it is placed in contact with the gel mixture. Drying can be accomplished by exposure to heat or to air. A particularly convenient drying method is to pass the coated plate through an infrared tunnel.

The foregoing description is primarily for purposes of illustration. Further modifications, substitutions and variations will be apparent to those skilled in the art and will be included within the scope of the invention.

What is claimed is:

1. A pre-cast polyacrylamide slab gel for use in slab gel electrophopresis, said pre-cast gel comprising:
   a pair of chemically inert, transparent plates of a member selected from the group consisting of glass and polystyrene-acrylonitrile blend with inner surfaces coated with a nonionic amphiphilic polymer; and
   a polyacrylamide gel cast between said plates.

2. A pre-cast polyacrylamide slab gel in accordance with claim 1 in which said nonionic amphiphilic polymer is polyvinyl alcohol.

3. A pre-cast polyacrylamide slab gel in accordance with claim 1 in which said plates are glass.

4. A pre-cast polyacrylamide slab gel in accordance with claim 1 in which said plates are polystyrene-acrylonitrile blend.

* * * * *